United States Patent [19]

Monical et al.

[11] Patent Number: 5,895,822

[45] Date of Patent: Apr. 20, 1999

[54] PROCESS FOR PURIFYING ACRYLONITRILE

[75] Inventors: Valerie S. Monical, Houston, Tex.; Daniel E. Steinmeyer, Chesterfield, Mo.; Gregory J. Ward, Gulf Breeze, Fla.

[73] Assignee: Solutia Inc., St. Louis, Mo.

[21] Appl. No.: 08/956,640

[22] Filed: Oct. 23, 1997

Related U.S. Application Data

[60] Provisional application No. 60/029,080, Oct. 23, 1996.

[51] Int. Cl.⁶ .................................................. C07C 253/00
[52] U.S. Cl. ......................................................... 558/320
[58] Field of Search ............................................. 558/320

[56] References Cited

U.S. PATENT DOCUMENTS 3,936,360  2/1976  Wu .............................................. 203/75

FOREIGN PATENT DOCUMENTS

| 0 000 566 A1 | 2/1979 | European Pat. Off. . |
| 0 053 518 A1 | 6/1982 | European Pat. Off. . |
| 40 39 177 A1 | 12/1990 | Germany . |

*Primary Examiner*—Johann Richter
*Assistant Examiner*—Joseph Murray
*Attorney, Agent, or Firm*—Arnold, White & Durkee

[57] ABSTRACT

The fouling rate of quench systems in acrylonitrile manufacturing processes is reduced by maintaining a low level of highboiling organic compounds in aqueous recycle streams to the quench systems.

8 Claims, 1 Drawing Sheet

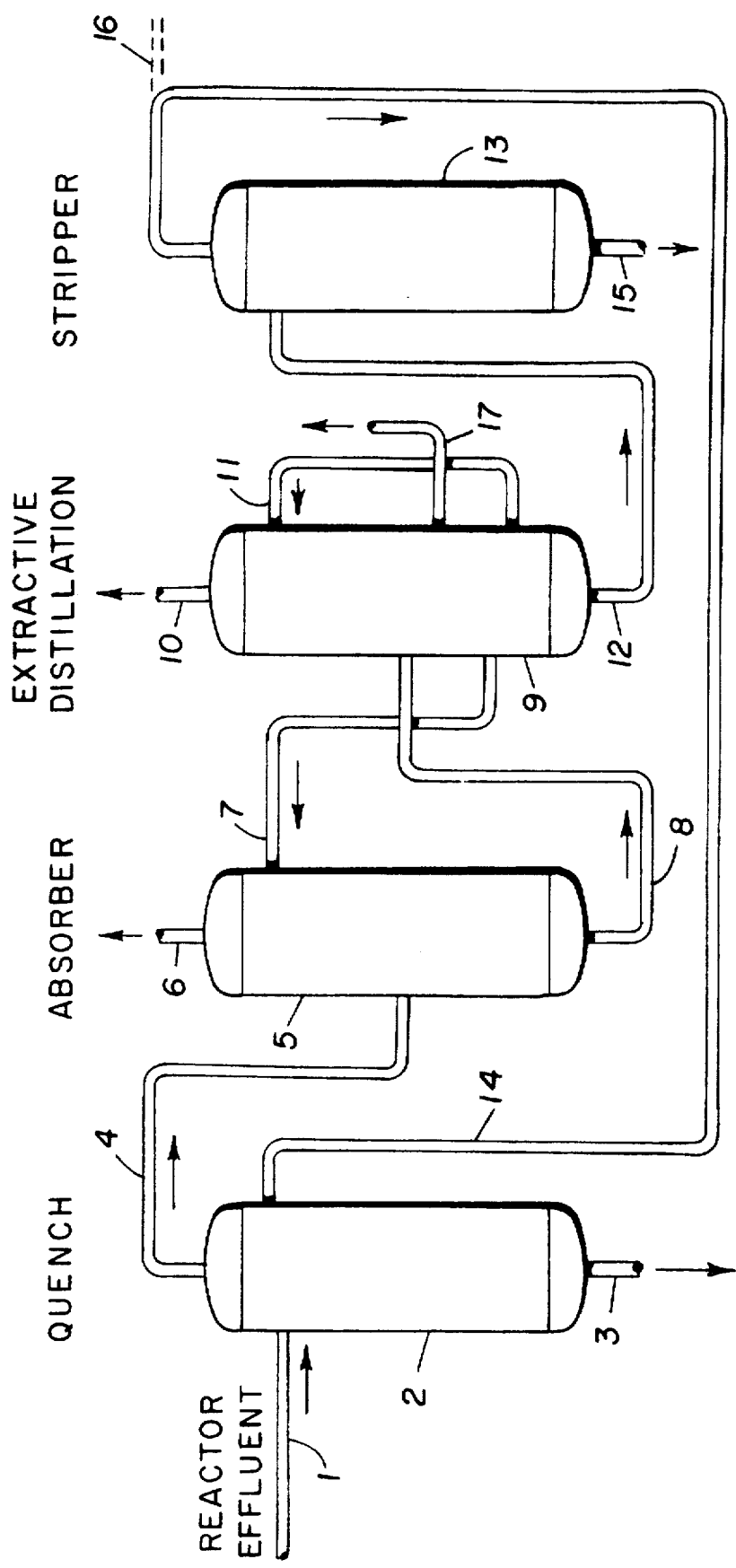

PROCESS FOR PURIFYING ACRYLONITRILE

This application claims the benefit of U.S. provisional application 60/029,080, filed on Oct. 23, 1996.

BACKGROUND OF THE INVENTION

This invention relates to the recovery and purification of acrylonitrile made by catalytic ammoxidation of propylene.

In commercial processes for preparation of acrylonitrile from propylene, ammonia, and oxygen (air), the reactor effluent contains, in addition to the desired acrylonitrile product, considerable amounts of by-product hydrogen cyanide, acetonitrile, and other impurities such as succinonitrile and other nitriles. The exact composition of the effluent and the by-products and impurities it contains may vary considerably depending on the ammoxidation reaction conditions and catalyst.

Processes for treating reactor effluents of the type described to separate and recover acrylonitrile product and desired by-products such as hydrogen cyanide and acetonitrile are known. For example, see U.S. Pat. Nos. 3,399,120; 3,433,822; 3,936,360; 4,059,492; 4,166,008; and 4,404,064, the disclosures of which are incorporated herein by reference. Typically, these processes include introducing the reactor effluent into a quench chamber where it is contacted with water (usually containing sulfuric acid to neutralize excess ammonia from the reaction) to cool the effluent and remove some contaminates such as polymers produced in the reactor. Cooled effluent gases from the quench flow to an absorber column where they are contacted with water. The liquid stream from the bottom of the absorber column contains most of the nitriles produced in the reaction and impurities and is sent to an extractive distillation column. The major portion of the acrylonitrile from the extractive distillation column is obtained in the overhead (distillate) from the column while water and impurities constitute the bottom stream from the column. In accordance with practices of the art, the bottom stream is frequently fed to a secondary distillation or stripper column to separate acetonitrile and water in an overhead stream while the secondary column bottoms containing water and various impurities are recycled to the quench column. It was apparently believed that the impurities in the recycle stream were acceptable in the quench system (see, for example, U.S. Pat. No. 3,960,360). The large quantity of quench liquid required by the quench column and waste management considerations make the appropriate use of recycle water an important process consideration. Accordingly, improvements in recycle practices are sought by those skilled in the art.

SUMMARY OF THE INVENTION

It has been found that the known practice of recycle of streams enriched in high boiling organic compounds, for example, stripper column bottoms, to the quench system promotes fouling. In accordance with the present invention, the high boiling organic compound content of liquid fed to quench is maintained at less than 5000 ppm. The invention further involves processes for minimizing contamination of recycle streams with high boiling organic impurities which are believed to contribute to quench column fouling. The invention will be understood from the drawing and the description of the preferred embodiments.

DESCRIPTION OF THE DRAWING

The drawing is a schematic representation of the present invention in the form of a simplified process flow diagram. For simplicity, various recycle streams and heat supply/recovery means which will generally be used in conjunction with the process are not shown.

DESCRIPTION OF THE PREFERRED EMBODIMENTS

The present invention can advantageously be used for processing of reactor product effluents from reactors in which acrylonitrile is produced by the catalytic ammoxidation of propylene. The commercial production of acrylonitrile by such reactions is well known. The product effluent of such reactions normally contains, in addition to acrylonitrile, by-product hydrogen cyanide, acetonitrile, acrolein, addition compounds of hydrogen cyanide and high boiling and resinous organic compounds. For purposes of this invention, the phrases "high boiling organic compounds" or "high boilers" are defined to include succinonitrile and organic compounds boiling at equal or higher temperatures than succinonitrile. Such materials are significant because it has been found that their recycle to the quench column contributes to quench column fouling. This is contrary to previous beliefs as expressed in U.S. Pat. No. 3,936,360, for example, that "the exact nature of these impurities is not critical because they have been found to be acceptable in the quench system".

In the process of the present invention, based on recognition of the detrimental effect of high boilers in the quench system, the high boiler content of quench liquid fed to the quench system is limited to 5000 ppm by weight.

High boiling organic compounds originate not only in the reactor but in other "make points" in the process system. In the quench system, for example, succinonitrile is made from the reaction of acrylonitrile and hydrogen cyanide. The formation of succinonitrile increases with increasing temperature and pH. Further formation of high boilers occurs in the system downstream of the quench. In fact, depending on variables such as temperature and acidity, the system downstream of the quench chamber is frequently the largest source of high boiler origin.

Since temperatures, acidity and other conditions in the primary reaction and product separation processes must be chosen, primarily, to facilitate product yield and recovery, the ability to select conditions for minimization of high boiler formation is limited. Therefore, as a practical matter, reducing the highboiler content of the quench liquid to reduce fouling requires proper selection of the source of quench liquid including, in some cases, process modifications to provide recycle streams of low highboiler content.

Quench liquid low in highboiler content is provided in one embodiment by feeding only "clean" water to the system. For example, fresh water or collected rain water or condensate water essentially free of heavy organics can be utilized. Alternatively, clean water can be used to dilute highboiler rich recycle streams to an acceptable highboiler concentration. However, such added water as well as water produced in the overall process must eventually be purged and intolerable or expensive waste disposal problems are likely when total process water is unduly increased. Consequently, the derivation of quench liquid from process recycle streams to the extent possible is normally desired. Preferred embodiments of the invention, therefore, constitute processes wherein quench liquid is at least in part derived from process recycle streams of low highboiler content.

The invention is described by reference to the drawing. However, those skilled in the art will appreciate that many variations of the specific separation process depicted are known and that the essence of this invention—reduction of highboilers fed to the quench system—can be beneficially applied to any such variation.

Turning to the drawing, in the present invention, as in conventional practice, the ammoxidation reactor effluent (which may be pre-cooled if desired) is passed through a conduit 1 into a quench column 2 where it is contacted with quench liquid introduced through line 14. (Although this drawing shows a quench column, the quench system may, alternatively, be any gas-liquid contact means such as, for example, Venturi towers, spray towers or the like.) This quench liquid is primarily water and is shown as being obtained as a distillate from a secondary stripper column hereinafter described. However, the quench liquid may be obtained in whole or part from other sources, not shown, if desired. As explained above, recycle quench liquid from process sources may be supplemented or replaced with "clean" water. It is preferred that 55% to 75% by weight of the quench liquid be recycled distillate. The requirement of this invention is that the quench liquid introduced into the quench system contain less than 5000 ppm by weight high boiling organic compounds. Preferably, the quench liquid will contain less than 2500 ppm high boiling organic compounds. In addition, sufficient sulfuric acid to neutralize any excess ammonia may be added. To minimize formation of highboilers in the quench system itself, the system is preferably operated at as low a temperature and pH as practicable, commensurate with other process considerations.

A bottoms stream containing water and, usually, high concentrations of organic impurities and sulfates exits the quench column through conduit 3 for disposal or further treatment while cooled reactor effluent gas exits through conduit 4 and is fed to an absorber column 5. This gas is contacted with water introduced through conduit 7. Noncondensable gases exit overhead through conduit 6 while an aqueous bottoms stream containing acrylonitrile, acetonitrile, and impurities exits through conduit 8 and is fed to an extractive distillation column 9. Preferably, the composition of aqueous stream 7 is controlled by selection of the source of this stream and control of the extractive distillation column discussed below and the temperature is also controlled in conventional manner such that the stream exiting through conduit 6 contains a major portion of any fumaronitrile and maleonitrile formed in the acrylonitrile reactor and a major portion of any cyanpropanal formed in the purification process. It is noted that the designs of extractive distillation columns are varied and frequently employ heat recovery devices and use recycle streams from point to point in the column or from other process units to optimize separation efficiency and/or economy. The design of this column and of the previously referenced quench and absorber columns are not critical to this invention and any commercially viable design can be utilized. In general, in extractive distillation columns, water is introduced through conduit 11 (usually located above the feed point of the bottoms stream from the absorber) to effect extractive distillation in the column which will normally contain 50–100 or more trays. To obtain optimum compositions for the preceding absorber column, the draw point of conduit 11 is, preferably, two to ten trays below the draw point of conduit 7. It is not essential that the draw point of conduit 11 be below that of conduit 7. However, it is important that there be at least five to forty trays below the lower of these points to assure organics such as fumaronitrile, maleonitrile, cyanpropanal and others of similar boiling point are purged to overhead exit points 6 and 10 rather than being allowed to accumulate for recycle in conduit 14 from the stripper. Acrylonitrile and hydrogen cyanide are removed overhead through conduit 10. Preferably, acetonitrile is removed from the extractive distillation column through conduit 17. This is not essential but, otherwise the overhead stream exiting the stripper through conduit 6 will contain significant amounts of acetonitrile.

In accordance with a preferred embodiment of the present invention, a bottom stream from the extractive distillation column containing water and impurities is removed through conduit 12 and fed to a secondary stripper column containing a plurality of stripper trays. This stream will be high in water content, sometimes up to 99% by weight. The stripper serves to split the stream from conduit 12 into a distillate which exits through conduit 14 and is low in highboilers and a bottom stream rich in highboilers which exits through conduit 15. The distillate can be recycled as quench liquid to the quench system to provide the low highboiler content quench liquid required by this invention. If the quantity of distillate is greater than needed/desired for recycle, all or part of the distillate stream can be diverted into conduit 16 (shown by dotted lines) for other uses, treatment or disposal. The low organic content of the stream will facilitate the use of biotreatment procedures. High boilers and water are removed through conduit 15 and may be disposed of or utilized in incinerator/fuel recovery processes or spent acid plants.

With regard to stripper design, the number of trays is not critical. Significant separation of high boiling organics can be obtained with from one to forty trays although little additional improvement is obtained by using more than five. It is preferred to introduce the feed to the top stripper tray since this provides maximum reduction of high boiling organics in the distillate exiting through conduit 14.

For purposes of the foregoing discussion, the stripper unit has been shown as a separate column. However, if preferred, the stripper can be physically integrated as part of the extractive distillation column. In commercial practice, conventional heat recovery practices will normally be utilized. For example, the distillate from a separate stripper column can be condensed in a heat exchanger to supply heat used in a reboiler for a separate extractive distillation unit.

Those skilled in the art will appreciate that all columns will be provided with necessary heat to effect their intended functions and that, for purposes of economy, much of such heat will be obtained from recycle streams used to supply processing liquid to the columns or to provide improved concentration/separation of various components. Such recycle and heat recovery techniques are conventional practice and, for simplicity, are not shown in the drawing or discussed in detail herein.

The invention is further illustrated by the following examples:

EXAMPLE 1

The product stream from the reaction of propylene with ammonia and air in the presence of an ammoxidation catalyst is cooled to a temperature of 232° C. and fed into a quench column. The composition of the product stream is 10.14% by weight acrylonitrile, 0.09% acetonitrile, 1.48% hydrogen cyanide, 0.07% acrolein, 0.33% heavy organic compounds, 3.85% CO and $CO_2$, 62.73% nitrogen, 3.46% oxygen, 0.44% propane, 0.09% propylene, 0.42% ammonia, 16.90% water per A. The product stream is contacted with an aqueous quench liquid which comprises the distillate from a stripper column hereinafter described to which sulfuric acid has been added. The quench liquid fed to the column contains less than 2500 ppm high boiling organic compounds. The feed rate of product stream to the quench column is 2988.54 kg/h and of quench liquid is 349.74 kg/h.

Condensed/dissolved components of the product are removed as an aqueous waste stream near the column bottom while uncondensed gaseous components are removed overhead and fed to an absorber column where they are contacted with water. The dissolved components are fed to an extractive distillation column where acrylonitrile is removed overhead, acetonitrile is removed as a sidestream, and high boiling organics and water are removed as a bottom stream and fed to the top tray of a stripper column containing 5 stripper trays. The composition of this feed is 0.6% by weight high boiling organic compounds and 99.4% water.

A bottom stream containing 10% by weight high boiling organic material is removed as waste and the distillate containing less that 2500 ppm high boiling organic materials is recycled as quench liquid to the quench column.

For comparison, the above procedure is repeated except that the bottom stream from the quench column is recycled as quench liquid instead of the distillate. More rapid fouling of the quench column is observed.

For further comparison, the first procedure is repeated except that the bottom stream from the extractive distillation column is fed to the bottom tray of the stripper column. The distillate is found to contain a higher concentration of high boiling organic components than when the feed is to the top tray.

What is claimed is:

1. In a process for purifying acrylonitrile in which an ammoxidation reactor effluent containing acrylonitrile and impurities is contacted in a quench system with an aqueous quench liquid; the improvement being that said quench liquid contains less than 5000 ppm by weight of high boiling organic compounds.

2. The process of claim 1 wherein at least a portion of said aqueous quench liquid is obtained from subsequent operations of the process.

3. In process for purifying acrylonitrile, said process comprising contacting an ammoxidation reactor effluent containing acrylonitrile and impurities in a quench system with an aqueous quench liquid; removing a gaseous effluent from the quench system and absorbing said gaseous effluent in water in an absorption column to form an aqueous solution; feeding said aqueous solution to an extractive distillation column having a plurality of trays; introducing water above the feed point of said aqueous solution and performing an extractive distillation to produce an overhead stream containing acrylonitrile and a bottom stream containing water and impurities; feeding the bottom stream from the extractive distillation column to a stripper column containing a plurality of stripper trays, removing water and high boiling organic compounds as a bottom stream from the stripper column, removing a water containing distillate as an overhead stream from the stripper column, and recycling distillate water to the quench column, the improvement being that the recycled distillate contains less than 5000 ppm by weight high boiling organic compounds.

4. The process of claim 3 wherein the distillate from the stripper column contains less than 2500 ppm of high boiling organic compounds.

5. The process of claim 3 wherein the bottom stream from the extractive distillation column is fed to the top stripper tray of the stripper column.

6. The process of claim 3 wherein the overhead stream from the stripper is passed through heat recovery means prior to recycle to the quench column.

7. The process of claim 3 further characterized in that a major portion of acetonitrile in the feed from the absorption column to the extractive distillation column is removed from the extractive distillation column in a side stream not fed to the stripper column.

8. The process of claim 3 wherein recycled distillate provides from 55% to 75% & by weight of the water in the aqueous quench liquid.

* * * * *